United States Patent
Matsumoto et al.

(10) Patent No.: US 7,857,165 B2
(45) Date of Patent: Dec. 28, 2010

(54) DISPENSING UNIT FOR MEASURING ARTICLES

(75) Inventors: Daisuke Matsumoto, Kyoto (JP); Tokuo Kasai, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 12/287,797

(22) Filed: Oct. 14, 2008

(65) Prior Publication Data

US 2009/0114673 A1    May 7, 2009

Related U.S. Application Data

(62) Division of application No. 10/505,910, filed as application No. PCT/JP03/02304 on Feb. 28, 2003, now Pat. No. 7,449,148.

(30) Foreign Application Priority Data

Feb. 28, 2002    (JP)    ............... 2002-054894

(51) Int. Cl.
  *B65H 1/00*    (2006.01)
  *B65H 3/24*    (2006.01)
(52) U.S. Cl. .............. 221/271; 221/197; 221/199; 221/268
(58) Field of Classification Search ............... 221/92, 221/97–99, 123, 124, 130, 175, 176, 197–199, 221/208, 239, 251, 254, 259, 268, 270, 271, 221/279, 280, 282, 287, 312 C
See application file for complete search history.

(56) References Cited

U.S. PATENT DOCUMENTS

| | | | | |
|---|---|---|---|---|
| 1,072,859 | A * | 9/1913 | Kingsley | 221/59 |
| 1,375,520 | A * | 4/1921 | Kingsley | 312/61 |
| 1,658,085 | A * | 2/1928 | Hudson | 206/494 |
| 4,872,593 | A * | 10/1989 | Behringer | 221/231 |
| 4,986,440 | A * | 1/1991 | Windorski | 221/45 |
| 5,030,418 | A | 7/1991 | Miyata | |
| 5,395,504 | A | 3/1995 | Saurer et al. | |
| 5,509,571 | A * | 4/1996 | Weber | 221/46 |
| 5,510,266 | A * | 4/1996 | Bonner et al. | 436/43 |
| 5,588,555 | A * | 12/1996 | Kanamori et al. | 221/197 |
| 5,854,074 | A | 12/1998 | Charlton et al. | |
| 5,894,927 | A * | 4/1999 | Bennett | 206/438 |
| 6,273,315 | B1 * | 8/2001 | McGuinness et al. | 227/18 |
| 6,827,899 | B2 | 12/2004 | Maisey et al. | |

(Continued)

FOREIGN PATENT DOCUMENTS

GB    2 001 443    1/1979

(Continued)

*Primary Examiner*—Gene Crawford
*Assistant Examiner*—Kelvin L Randall, Jr.
(74) *Attorney, Agent, or Firm*—Hamre, Schumann, Mueller & Larson, P.C.

(57) ABSTRACT

A measuring instrument (A) includes: a storage (1) which has an insertion port (10) for insertion of measuring articles (S) and is capable of storing the measuring articles stacked in a direction of the insertion; and movable members (2A, 2B) for a movement of dispensing a predetermined quantity of the measuring articles (S) out of the storage (1) toward a measuring position (P). With such an arrangement, refilling of the measuring articles (S) to the measuring instrument (A) becomes easy, and the measuring instrument (A) can be always loaded suitably with a quantity of the measuring articles.

2 Claims, 18 Drawing Sheets

U.S. PATENT DOCUMENTS

| | | | |
|---|---|---|---|
| 6,872,358 B2 | 3/2005 | Hagen et al. | |
| 6,881,578 B2 | 4/2005 | Otake | |
| 6,908,008 B2 * | 6/2005 | Pugh | 221/135 |
| 6,997,343 B2 | 2/2006 | May et al. | |
| 7,063,234 B2 * | 6/2006 | Giraud | 221/271 |
| 2002/0076349 A1 * | 6/2002 | Aitken et al. | 422/58 |
| 2002/0104849 A1 * | 8/2002 | Giruad | 221/270 |
| 2002/0162847 A1 * | 11/2002 | Roy | 221/34 |
| 2003/0089730 A1 * | 5/2003 | May et al. | 221/232 |
| 2004/0007585 A1 * | 1/2004 | Griffith et al. | 221/232 |

FOREIGN PATENT DOCUMENTS

| | | |
|---|---|---|
| JP | 6-294769 | 10/1994 |
| JP | 8-94630 | 4/1996 |
| JP | 8-262026 | 10/1996 |
| JP | 9-250998 | 9/1997 |
| JP | 10-253570 | 9/1998 |
| JP | 2001-141686 | 5/2001 |
| JP | 2001-281199 | 10/2001 |
| JP | 2003-42994 | 2/2003 |
| WO | WO 94/10558 | 5/1994 |
| WO | WO 01/63272 | 8/2001 |
| WO | WO 02/08753 | 1/2002 |

* cited by examiner

DISPENSING UNIT FOR MEASURING ARTICLES

TECHNICAL FIELD

The present invention relates to measuring instruments and related techniques used in such an application as measuring the glucose level in human blood.

BACKGROUND ART

People suffering from diabetes should preferably perform periodic measurement on his/her blood glucose level so that appropriate prescription or other treatments can be arranged in response to the measuring results. A conventional example of a measuring instrument for this purpose is disclosed in JP-A 8-262026.

As shown in FIG. 19, this conventional instrument includes a casing 90 having an upper surface provided with a control 91, upon operation of which part of a sensor S projects out of an opening 90a from a tip of the casing 90. The sensor S is a small piece containing a reagent which reacts with glucose in the blood. When the sensor S makes contact with the blood of the user, a measurement circuit (not illustrated) in the casing 90 measures a glucose level in the blood, and a result of the measurement is displayed in a display 92.

The casing 90 accommodates a cartridge or a package 95 as shown in FIG. 20. The package 95 includes a package substrate 95a having a plurality of radial recesses 96 each holding a sensor S, and a film 95b covering an upper surface of the package substrate 95a. The package 95 is rotatable when attached in the casing 90, and the rotating action changes positions of the sensors S. In conventional measuring instruments, the film 95b of the package 95 is partially cut with an appropriate blade for example, and then the sensors S are pushed through this cutout by a predetermined pusher, sequentially one after another toward the opening 90a of the casing 90.

According to such a construction, it is possible to use each of the sensors S in the package 95, sequentially one at a time after another, and to perform a plurality of measurements of the blood glucose level.

However, according to the conventional art, it is not possible to easily refill as many sensors S as needed into the package 95 when the sensors S in the package 95 are running short. Therefore, it is not easy to always have the measuring instrument loaded with a sufficient number of sensors beyond a certain quantity. This is inconvenient. In order to load the measuring instrument with the sensors S, replacement must be made with a whole new package 95, and a lot of sensors S would be wasted if the replacement is made with a whole new package while the current package 95 still has unused sensors S.

DISCLOSURE OF THE INVENTION

An object of the present invention is to provide a measuring instrument capable of solving or reducing the above problem. Another object of the present invention is to provide a measuring article storing case and an operating-mechanism suitable for use in such a measuring instrument.

A first aspect of the present invention provides a measuring instrument which comprises a measurement circuit capable of performing a measuring operation using a measuring article when the measuring article is set to a predetermined measuring position. The instrument further comprises a storage having an insertion port for insertion of a plurality of the measuring articles and capable of storing the measuring articles stacked in a direction of the insertion; and a movable member for a movement of dispensing a predetermined quantity of the measuring articles out of the storage toward the measuring position.

Preferably, the storage allows stacking of the measuring articles in the order the measuring articles are inserted. Further, the movable member dispenses those of the measuring articles which are farthest from the insertion port in the storage, to the measuring position.

Preferably, the measuring instrument further comprises a reference surface in the storage, and an urger for urging the articles in the direction of the insertion in the storage to thereby bring the measuring article farthest from the insertion port into contact with the reference surface. Further, the movable member is reciprocatable across the direction of the insertion and capable of pushing the measuring article on the reference surface toward the measuring position.

Preferably, the measuring instrument according to the present invention further comprises a lid capable of opening and closing the insertion port. The lid includes the urger, allowing the insertion of the measuring articles into the storage when the insertion port is opened while allowing the urger to urge the measuring articles in the direction of the insertion when the insertion port is closed.

Preferably, the measuring instrument according to the present invention further comprises a base member supporting the storage and guiding the movable member in movement. The base member is formed with a slit for part of the movable member to pass through. The storage has a wall formed with a discharge port and a cutout recess facing with each other and communicating with the slit. The movable member enters the storage from the cutout recess and thereby pushes the measuring article in the storage from the discharge port.

Preferably, the measuring instrument according to the present invention further comprises a pair of contact plates sandwiching a path of the movable member in the storage and being urged toward the insertion port by a force weaker than an urging force of the urger. Each contact plate has a surface facing the insertion port and serving as the reference surface.

Preferably, the measuring instrument according to the present invention further comprises a stopper at an edge of the insertion port of the storage. The stopper allows insertion of the measuring articles from outside of the storage to inside thereof while preventing the measuring articles from escaping out of the storage.

Preferably, the stopper is an elastically deformable projection extending inwardly of the insertion port.

Preferably, the storage can be inserted by a case loaded with a plurality of the measuring articles stacked in a direction of thickness, for transfer of the measuring articles from the case to the storage through the insertion port.

Preferably, the measuring instrument according to the present invention further comprises a casing which accommodates the movable member and the measurement circuit and is formed with an opening for exposure of the measuring article. The movable member makes a first movement of bringing the measuring article to the measuring position thereby exposing part of the measuring article from the opening, and a second movement of discharging the measuring article from the opening, out of the casing.

Preferably, the measuring instrument according to the present invention further comprises a connector electrically connected with the measurement circuit and brought by the first movement to contact with the measuring article. The contact of the measuring article with the connector initiates a predetermined measuring operation using the measurement circuit.

A second aspect of the present invention provides a measuring article storing case for storage of a plurality of measuring articles which are to be loaded in a storage of a measuring instrument. The storage comprises a wall having a lower end formed with an insertion port. The case includes a bottom capable of supporting the measuring articles, a tubular side wall raised from an edge of the bottom, and an upper opening. At least one of the bottom and the side wall is provided with a series of ribs for maintaining an orderly state of stacking by preventing the stack of measuring articles stacked on the bottom in a direction of thickness from being out of position.

Preferably, the ribs and the measuring articles are spaced from each other for insertion of the wall of the measuring instrument.

Preferably, the wall of the measuring instrument has a lower end formed with a stopper extending inward of the insertion port. The bottom is formed with a raised table for placement of the stack of measuring articles. The table has an area smaller than an area of each measuring article, so the placement of the measuring articles on the table causes the measuring articles to overhang the table, forming a space beneath the overhang for the stopper.

A third aspect of the present invention provides a measuring instrument which comprises: a storage for storing a measuring article; a movable member capable of dispensing the measuring article to a predetermined measuring position; a measurement circuit capable of performing a measuring operation using the measuring article when the measuring article is set to the measuring position; and a casing accommodating the movable member and the measurement circuit, and formed with an opening for exposing the measuring article. The movable member makes a first movement of bringing the measuring article to the measuring position thereby exposing part of the measuring article from the opening, and a second movement of discharging the measuring article from the opening, out of the casing.

Preferably, the measuring instrument according to the present invention further comprises: a base member for guiding the movable member in movement; a cam groove formed in the base member; and a projection provided in the movable member and fitted into the cam groove. The cam groove controls a movement of the projection, bringing the movable member closer to the opening of the casing in the second movement than in the first movement.

A fourth aspect of the present invention provides an operating mechanism which comprises a base member and a movable member reciprocating on the base member. The base member is formed with a cam groove, while the movable member is formed with a projection fitted into the cam groove for movement in crosswise directions of the reciprocation of the movable member. The cam groove includes a plurality of forward movement grooves for a plurality of forward movements of the movable member, and these forward movement grooves extend forward by different distances.

Preferably, the operating mechanism according to the present invention further includes an elastic member which urges the projection in a crosswise direction of the reciprocation.

Other characteristics and advantages of the present invention will become clearer from the description of the mode of embodiment to be given hereafter.

BEST MODE FOR CARRYING OUT THE INVENTION

Hereinafter, a preferred mode for carrying out the present invention will be described specifically, with reference to the drawings.

Figure 1:
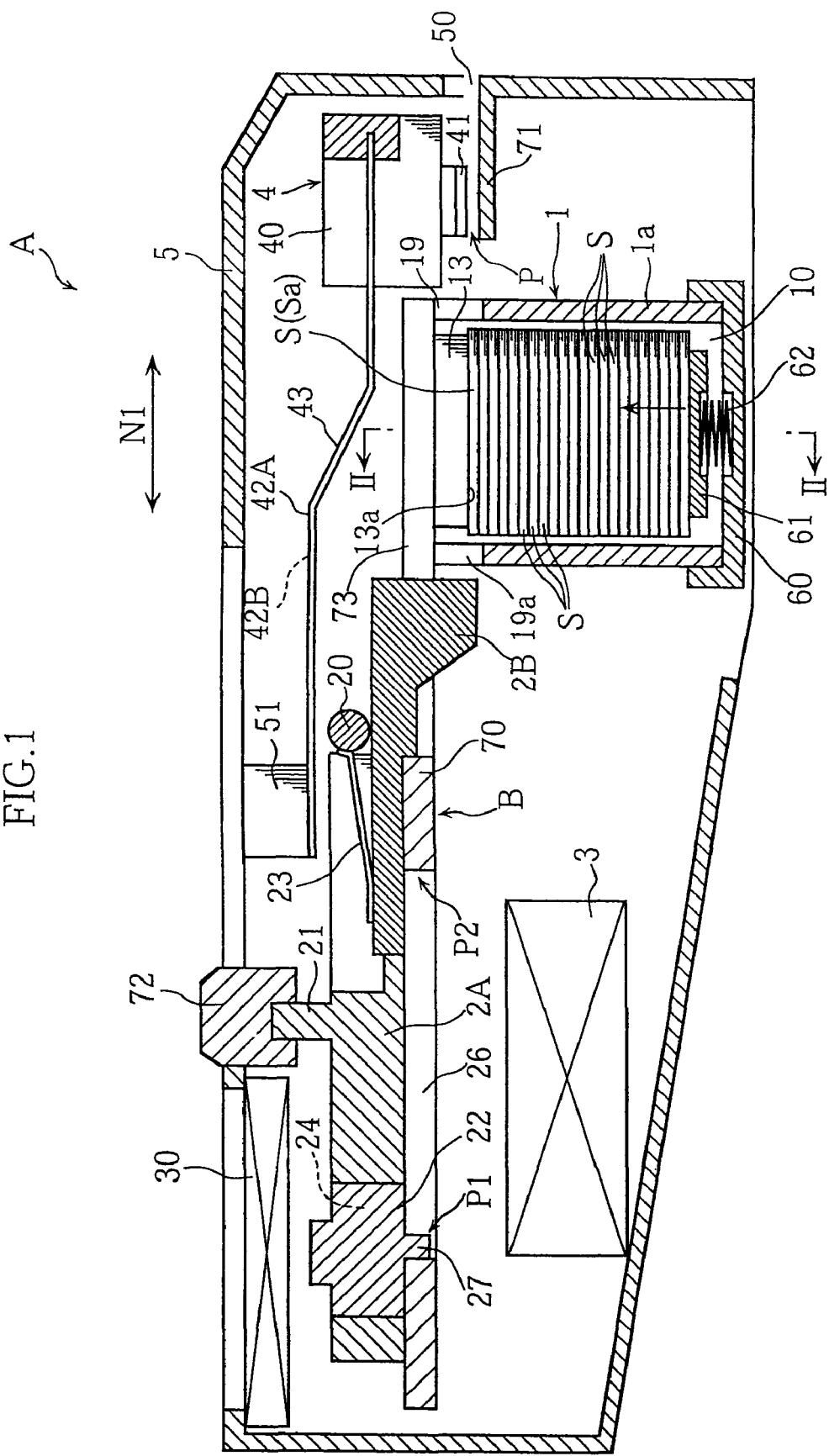
FIG. 1 is a simplified sectional view of a measuring instrument as an embodiment of the present invention.

FIG. 1 shows a measuring instrument according to the present invention. A measuring instrument A according to the present invention includes a storage 1 for storing a plurality of sensors S, a sensor dispensing mechanism B for taking a sensor S out of the storage 1, a measurement circuit 3, a connector 4, and a casing 5 which houses all of these. The sensor S is a small piece containing a reagent which reacts with glucose and a pair of electrodes (none illustrated) contacting the reagent.

The storage 1 is like a box, capable of storing a stack of sensors S, and has a wall 1$a$ in the form of a rectangular tube. According to the present invention however, the tubular wall may not be rectangular. Further, the tubular wall may not essentially be tubular, and may be formed with e.g. a plurality of longitudinal slits dividing the tube into a plurality of strip pieces. The wall 1a has an upper end connected to a lower surface of a base member 70 fixed in the casing 5.

The storage 1 has a lower portion formed with an insertion port 10. The insertion port 10 can be opened and closed by a lid 60 which is detachable from the storage 1. The lid 60 can be made detachable from the storage 1 by forming e.g. an engagable/disengageable pair of a recess and a projection on the lid 60 and on the lower portion of the storage 1. The lid 60 has a contact plate 61 which makes contact with the lowermost sensor S of the stack of sensors S loaded in the storage 1, and a spring 62 for urging the contact plate 61 in an upward direction. These members work to provide a constant upward urge to the sensors S in the storage 1. The wall 1a of the storage 1 has an upper portion formed with a discharge port 19 for discharging a sensor S to a side of the storage 1, and a cutout recess 19a facing the port. The cutout recess 19a provides a passage for a second movable member 2B to be described later.

Figure 2:
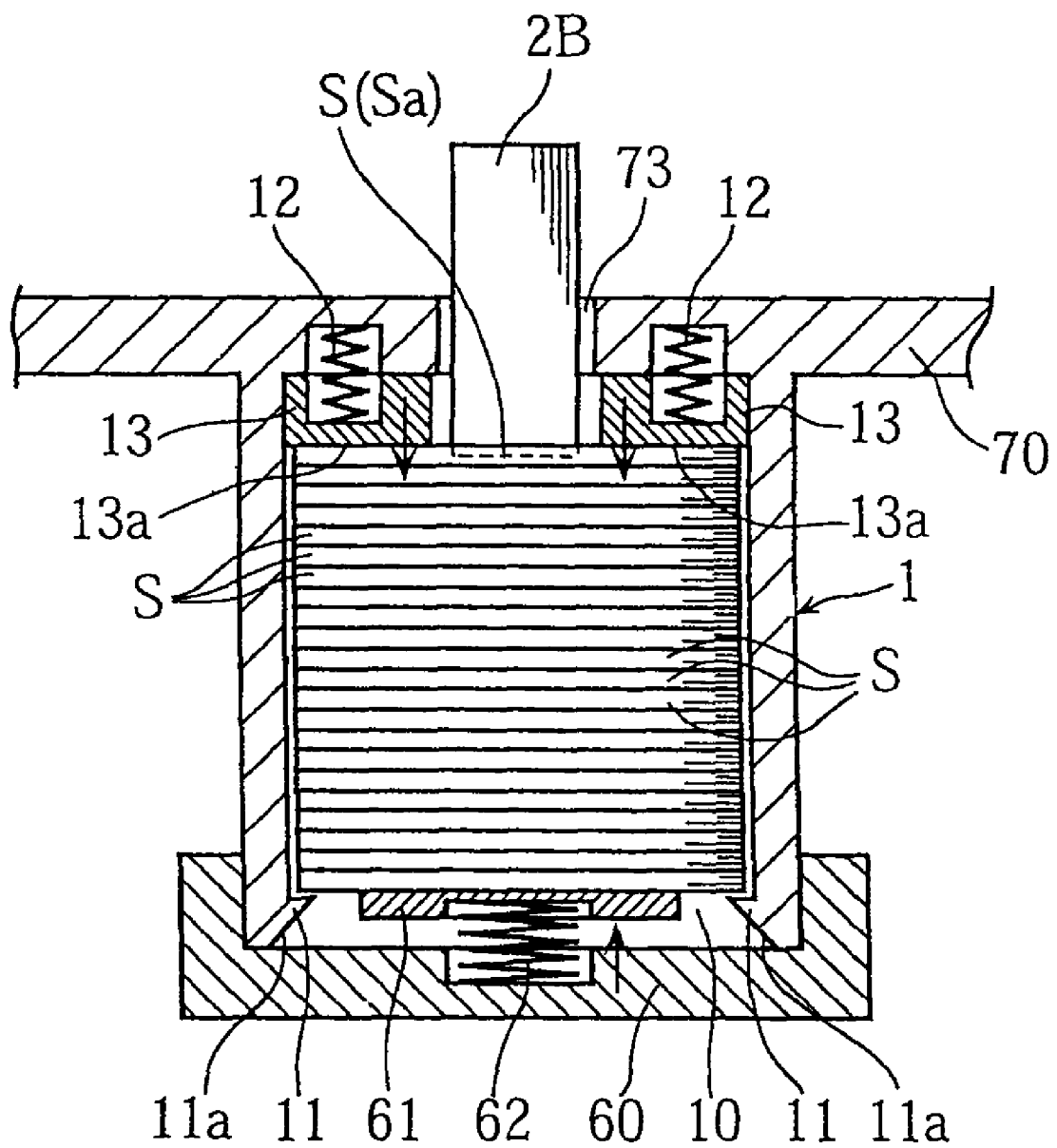
FIG. 2 is a sectional view taken in lines II-II in FIG. 1.

As clearly shown in FIG. 2, the storage 1 has a lower portion provided with an opposed pair of stoppers 11. Each stopper 11 prevents the sensors S loaded in the storage 1 from dropping out of the insertion port 10, and is formed as a projection out of an inner wall of the storage 1 protruding inwardly of the storage 1. Each stopper 11 is elastic, allowing insertion of sensors S from beneath the insertion port 10 into the storage 1. Further, each stopper 11 has a lower portion formed with a tapered surface 11a, which allows smooth insertion of the sensors S. The storage 1 also includes a pair of contact plates 13, not interfering with but sandwiching a stroke path of the second movable member 2B. Each contact plate 13 is constantly urged downward by a spring 12, so that the sensors S in the storage 1 is always under a downward urge from the spring 12. This elastic urge is smaller than the elastic urge from the spring 62. Therefore, when the lid 60 is attached to the lower portion of the storage 1, the contact plates 13 are always pressed upward by the elastic urge of the spring 62, to make contact with the lower surface of the base member 70. The contact plates 13 have downward facing surfaces 13a serving as a reference surface which is contacted by the uppermost sensor S (Sa) of the sensors S loaded in the storage 1, thereby controlling the height at which the sensor S (Sa) is held.

Referring to FIG. 1, the connector 4 includes a block 40 made of resin for example, which has a lower surface formed with metal terminals 41 for making contact with the pair of electrodes of the sensor S. The measurement circuit 3 includes a CPU, a memory and other relevant components, and is electrically connected to the connector 4. With the connector 4 electrically connected to the electrodes of a sensor S, and the sensor S having its reagent wetted by a human blood, the measurement circuit 3 is capable of obtaining a glucose level in the blood, based on variation etc. of an electric current passed through the reagent after the blood is introduced. Values of the glucose level and other information obtained by the measurement circuit 3 are displayable by a display 30. The display 30 is provided by a liquid crystal panel for example, and the display screen is visible from outside the casing 5.

Below the connector 4 is a support 71 for supporting a sensor S which has been dispensed from the storage 1. An area on the support 71 includes a measuring position P for the measurement of the glucose level using the sensor S. On a portion of the casing 5 on one side of the measuring position P, there is formed an opening 50 for having the sensor S exposed to outside of the casing 5 and discharged from inside thereof.

Figure 3:
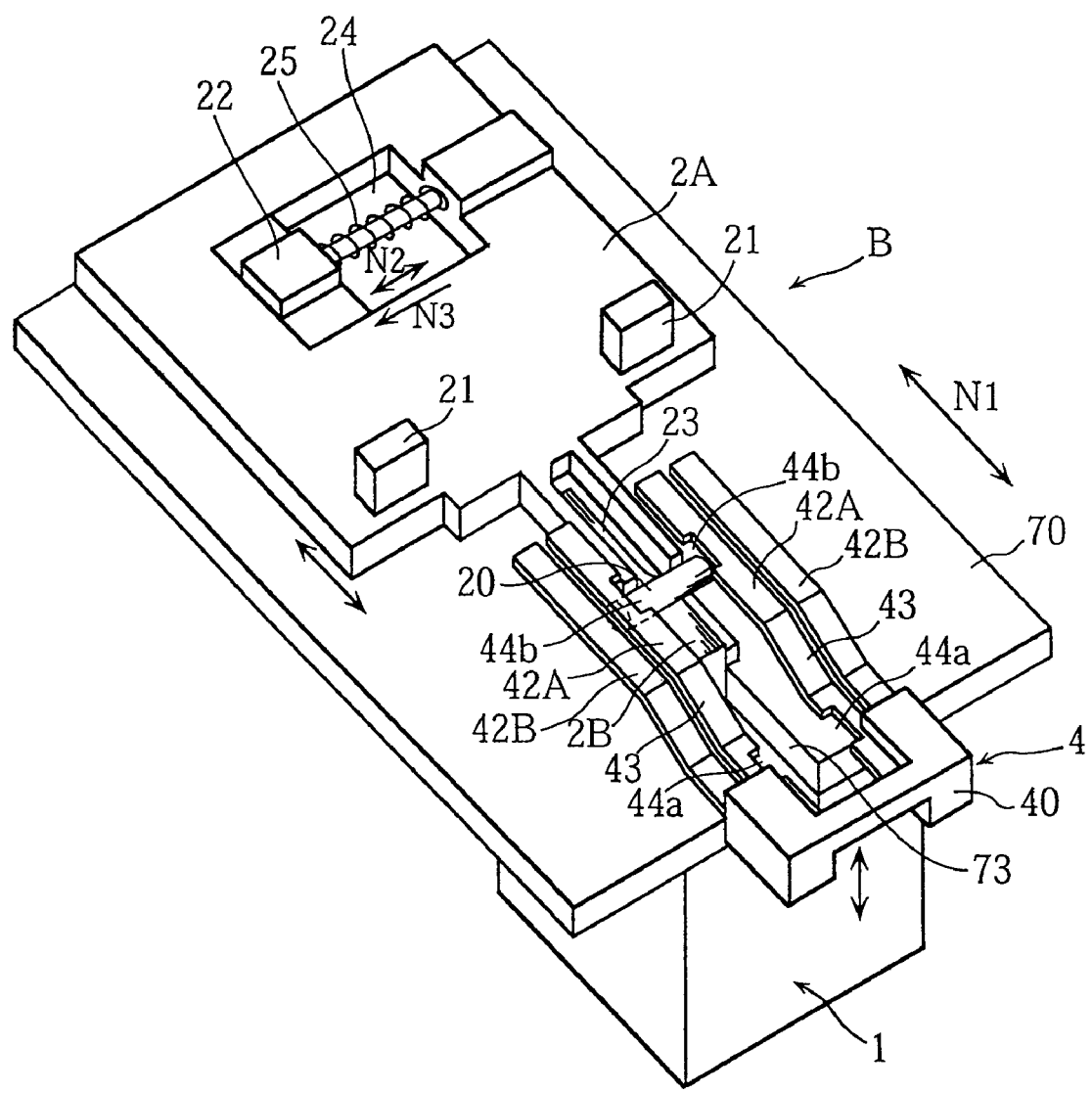
FIG. 3 is a simplified perspective view of a sensor dispensing mechanism used in the measuring instrument in FIG. 1.

The connector 4 is supported by a pair of first leaf springs 42A and a pair of second leaf springs 42B as shown in FIG. 3. These first and the second leaf springs 42A, 42B are of a cantilever structure, i.e. having their respective one end attached to e.g. an upper wall of the casing 5 via a bracket 51 (See FIG. 1), and extending in longitudinal directions N1 of the measuring instrument A. Although not illustrated in the drawings, the second leaf springs 42B are electrically connected to the terminals 41 of the connector 4, serving as part of wiring which establishes electrical connection of the terminals 41 to the measurement circuit 3. The terminals 41 can be formed integrally with the second leaf springs 42B by using appropriate parts of the second leaf springs 42B. Alternatively, the connector 4 can be supported by only the first leaf springs 42A, in which case electrical connection between the connector 4 and the terminals 41 may be achieved by electric wires instead of the second leaf springs 42B.

The first leaf spring 42A has a ramp 43 in its longitudinally intermediate portion, and a first and a second cutouts 44a, 44b sandwiching the ramp 43 from front and rear. As will be described later, these portions work with a pusher 20, helping the connector 4 to do predetermined rising and lowering actions.

The sensor dispensing mechanism B includes a first and a second movable members 2A, 2B, and a movable block 22. The first movable member 2A has a pair of projections 21 for engagement with an operating tab 72 which is on the upper surface of the casing 5, and is capable of reciprocating in the longitudinal directions N1 of the measuring instrument A, on the base member 70 when operated via the operating tab 72. The second movable member 2B is ahead (on the right side as in FIG. 1) of the first movable member 2A, and is capable of reciprocating together with the first movable member 2A in the same directions. The first and the second movable members 2A, 2B may be formed integrally with each other. The base member 70 supports the storage 1, and in addition guides the first and the second movable members 2A, 2B in their sliding movement, having also a slit 73 which communicates with the discharge port 19 and the cutout recess 19a of the storage 1. The second movable member 2B is capable of passing through the slit 73, the cutout recess 19a and the discharge port 19, thereby capable of pushing an uppermost sensor S (Sa) in the storage 1 toward the measuring position P. On the second movable member 2B, a pusher 20 is supported via a leaf spring 23. The pusher 20 is columnar for example, and is displaceable in vertical directions, causing the leaf spring 23 to deform elastically.

Figure 4:
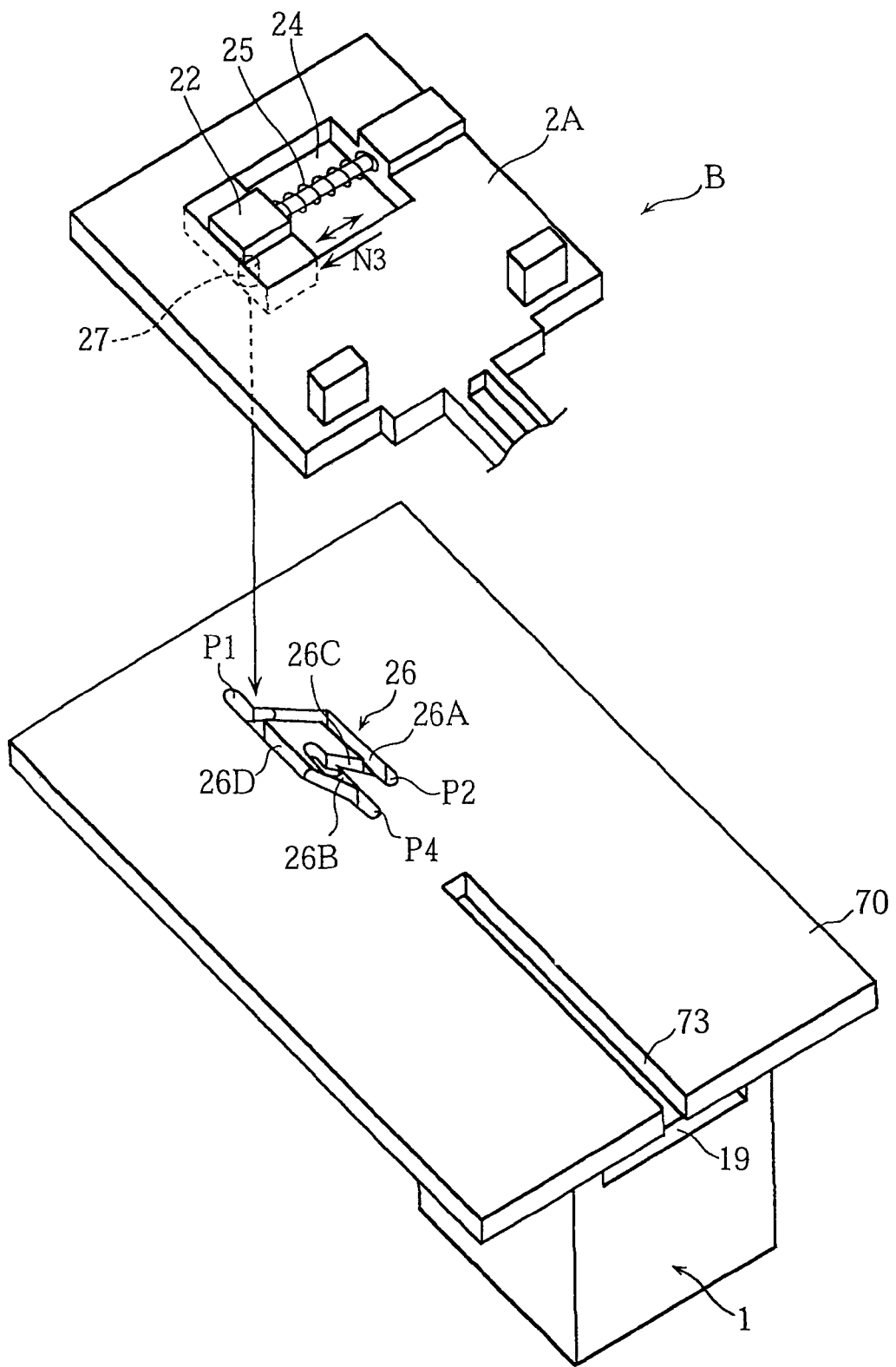
FIG. 4 is an exploded perspective view of a primary portion of the sensor dispensing mechanism used in the measuring instrument in FIG. 1.

As shown clearly in FIG. 3, the movable block 22 fits in an opening 24 formed in the first movable member 2A and is movable in widthwise directions N2 of the measuring instrument A. The movable block 22 is constantly urged by a spring 25 in a direction indicated by Arrow N. As shown clearly in FIG. 4, the base member 70 is provided with a cam groove 26 whereas the movable block 22 has a bottom surface formed with a downward facing projection 27 which fits in the cam groove 26. Combination of the projection 27 and the cam groove 26 provides an operating mechanism which controls the reciprocating action of the first and the second movable members 2A, 2B.

Figure 5:
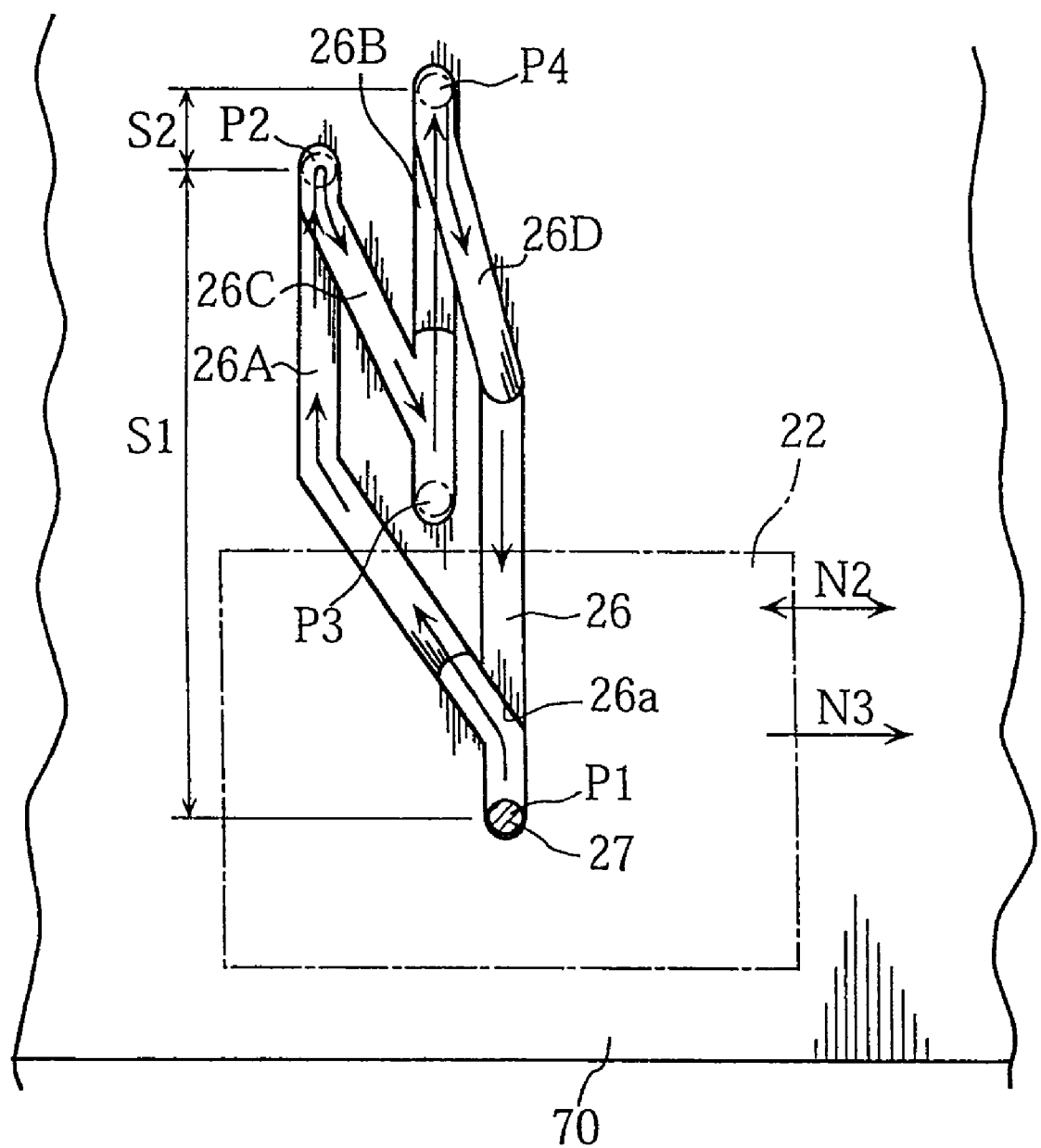
FIG. 5 is a plan view of a primary portion in FIG. 4.

The cam groove 26 is shaped as shown in FIG. 5. The upward direction in FIG. 5 is the forward direction of the measuring instrument A. When the first and the second movable members 2A, 2B are at their most rearward positions, the projection 27 is at a first position P1 in the cam groove 26. When the first and the second movable members 2A, 2B are reciprocated, the projection 27 moves forward for a predetermined distance S1 or to a second position P2 in the cam groove 26, and then moves back to a third position P3, and then forward to a fourth position P4, before coming back to the first position P1. With such an arrangement, a cycle of moving actions of the first and the second movable members 2A, 2B includes two forward movements. In the cam groove 26, a path 26A from the first position P1 to the second position P2 is a groove for the first forward movement while a path 26B from the third position P3 to the fourth position P4 is for the second forward movement. The cam groove 26 also includes a plurality of grooves having different lengths, for the rearward movements: A path 26C from the second position P2 to the third position P3 is for the first rearward movement while a path 26D from the fourth position P4 to the first position P1 is for the second rearward movement.

The fourth position P4 is ahead of the second position P2 by a predetermined dimension S2. This allows the first and the second movable members 2A, 2B to reach a farther point in their second forward movement than in the first forward movement of the first and the second movable members 2A, 2B. When the projection 27 moves in widthwise directions N2, the movable block 22 moves in the widthwise directions N2, while the first movable member 2A will not move together in the same directions. As has been described, the movable block 22 is constantly urged by the spring 25 in the direction N3. Thus, when the projection 27 moves from the second position P2 to the third position P3, and when moving back from the fourth position P4 to the first position P1, the projection 27 moves in the direction N3 under the urge, making sure that these actions happen reliably. The projection 27 is contacted and guided by a wall 26a formed in the cam groove 26 when moving forward from the first position P1, so that it will not move toward the fourth position P4.

Figure 6:
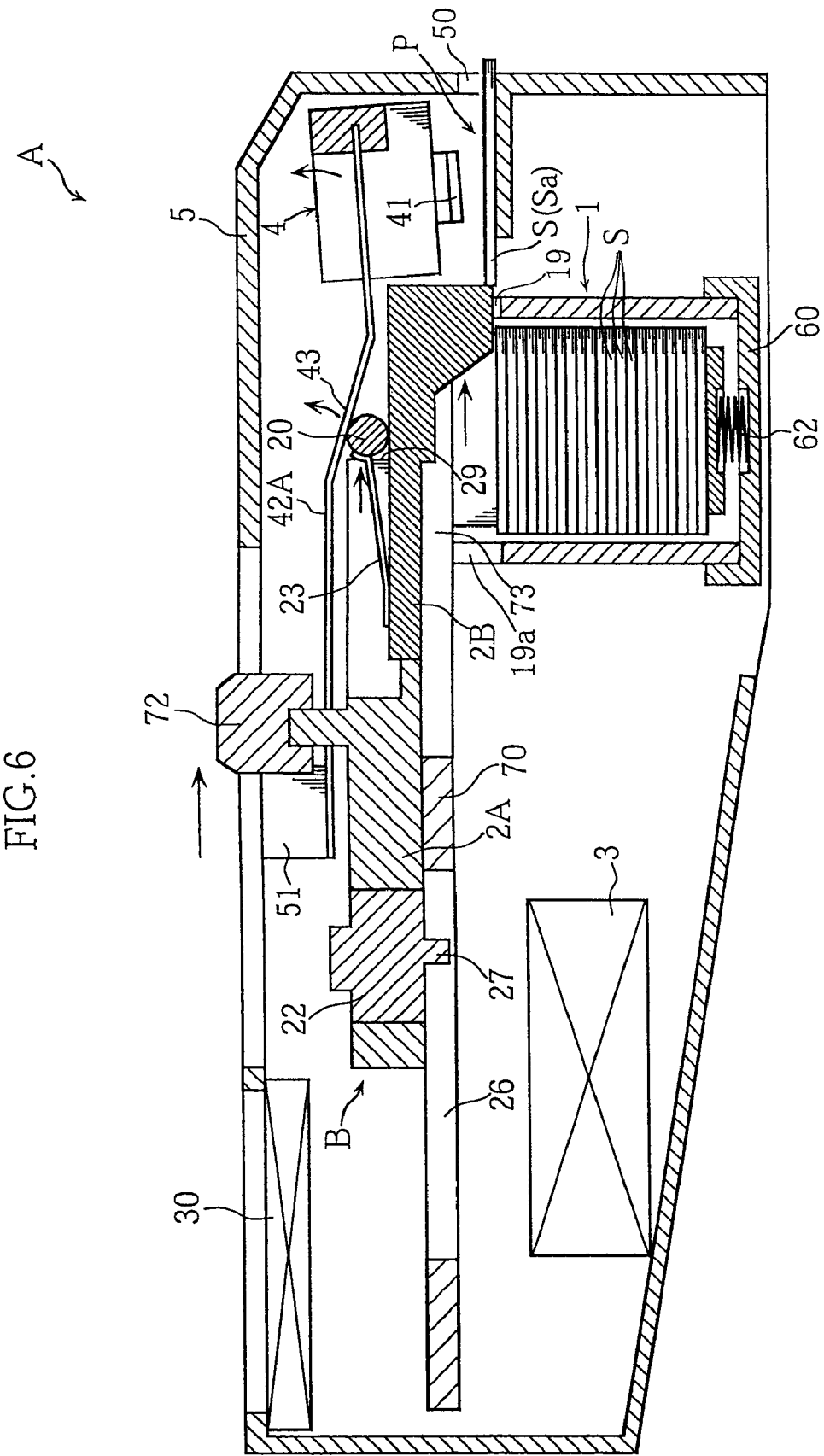
FIG. 6 is a simplified sectional view showing an action of the measuring instrument in FIG. 1.

The sensor dispensing mechanism B operates in the following actions, in relation with other portions such as the storage 1 and the connector 4:

Specifically, as shown in FIG. 6, when the operating tab 72 is operated in the forward direction, the first and the second movable members 2A, 2B move forward, with the second movable member 2B having its tip pass through the slit 73 and an upper portion of the storage 1. In this action, the second movable member 2B pushes an uppermost sensor S (Sa) in the storage 1 in the forward direction of the storage 1 to the measuring position P. As the second movable member 2B moves forward, the pusher 20 presses a lower surface of the ramp 43 of the first leaf springs 42A. With the pusher 20 placed on the upper surface of the second movable member 2B, and with the pusher 20 having its rear making contact with an appropriate wall 29 of the first movable member 2A, it is possible to press the ramp 43 appropriately in the forward direction without causing the pusher 20 to lower or retract. When the pusher 20 presses the lower surface of the ramp 43, each first leaf spring 42A deforms upward to raise the connector 4. Therefore, when a sensor S (Sa) is delivered to the measuring position P, the sensor S (Sa) will not make contact with the terminals 41, which protects the terminals 41 from wear.

Figure 7:
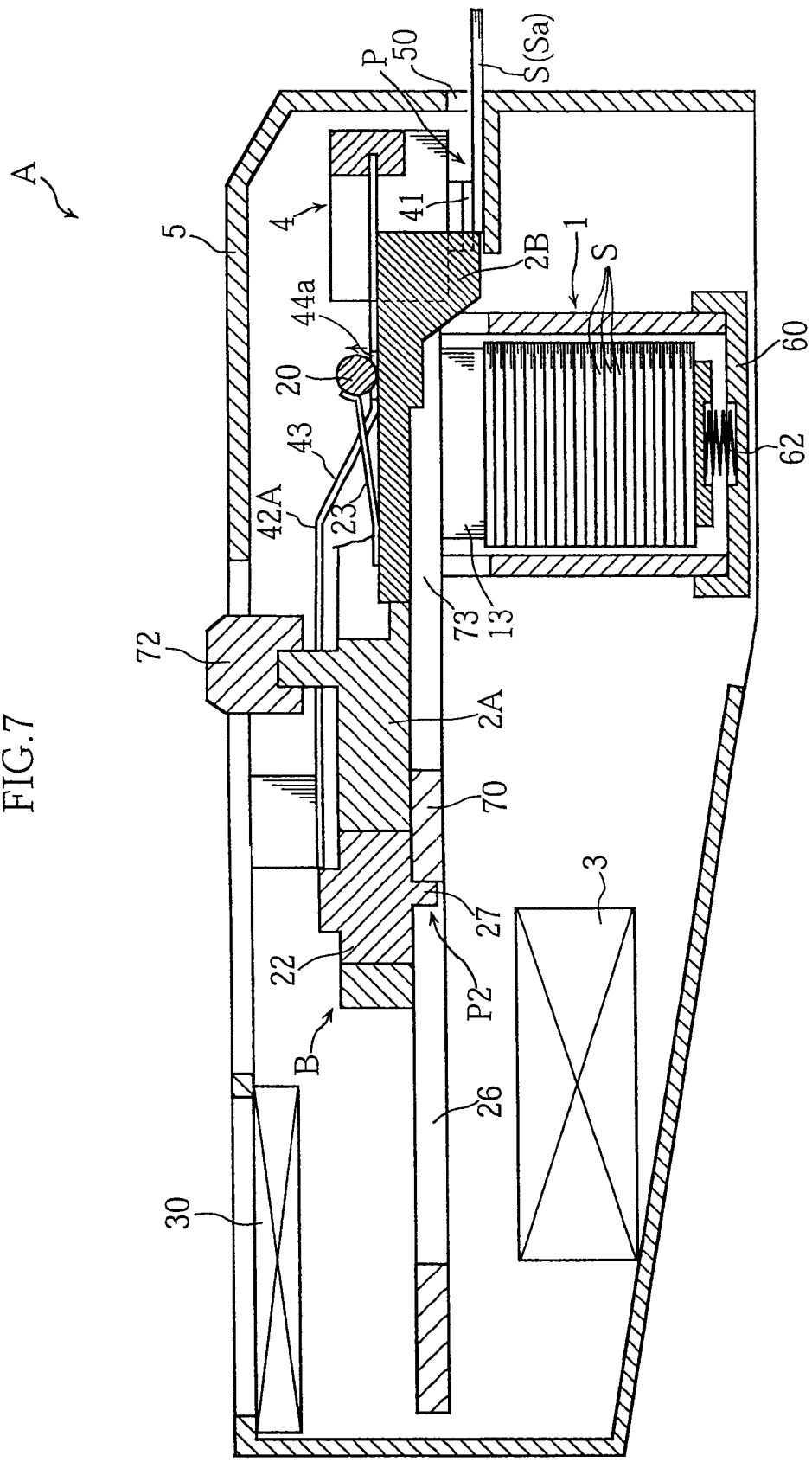
FIG. 7 is a simplified sectional view showing an action of the measuring instrument in FIG. 1.

Next, as shown in FIG. 7, when the first and the second movable members 2A, 2B move forward to bring the projection 27 to the second position P2 of the cam groove 26, the pusher 20 reaches where the first cutouts 44a are formed in the first leaf springs 42A, passes this place and thereby moves above each of the leaf springs 42A. Thus, the pusher 20 no longer presses up the first leaf springs 42A, which allows the connector 4 to come down to the initial height. In the above described forward movement, the second movable member 2B makes the sensor S move forward further, causing part of the sensor S projecting out of the casing 5, from the opening 50. Such a forward movement of the first and the second movable members 2A, 2B is the first forward movement of the described with reference to FIG. 5. Successively, in order to make the second forward movement, the projection 27 of the movable block 22 is first moved rearward to the third position P3. This rearward movement can be generated easily by an elastic urge for example, provided by a constant rearward urge from an elastic member such as a spring (not shown), exerted on the first and the second movable members 2A, 2B. Alternatively, this rearward movement may be done manually. The path 26C from the second position P2 to the third position P3 in the cam groove 26 is short and the amount of movement of the first and the second movable members 2A, 2B is small. This makes possible that the amount of forward movement of the first and the second movable members 2A, 2B after this rearward movement is small, and so the sensor S can be discharged quickly by a small amount of operation of the operating tab 72.

Figure 8:
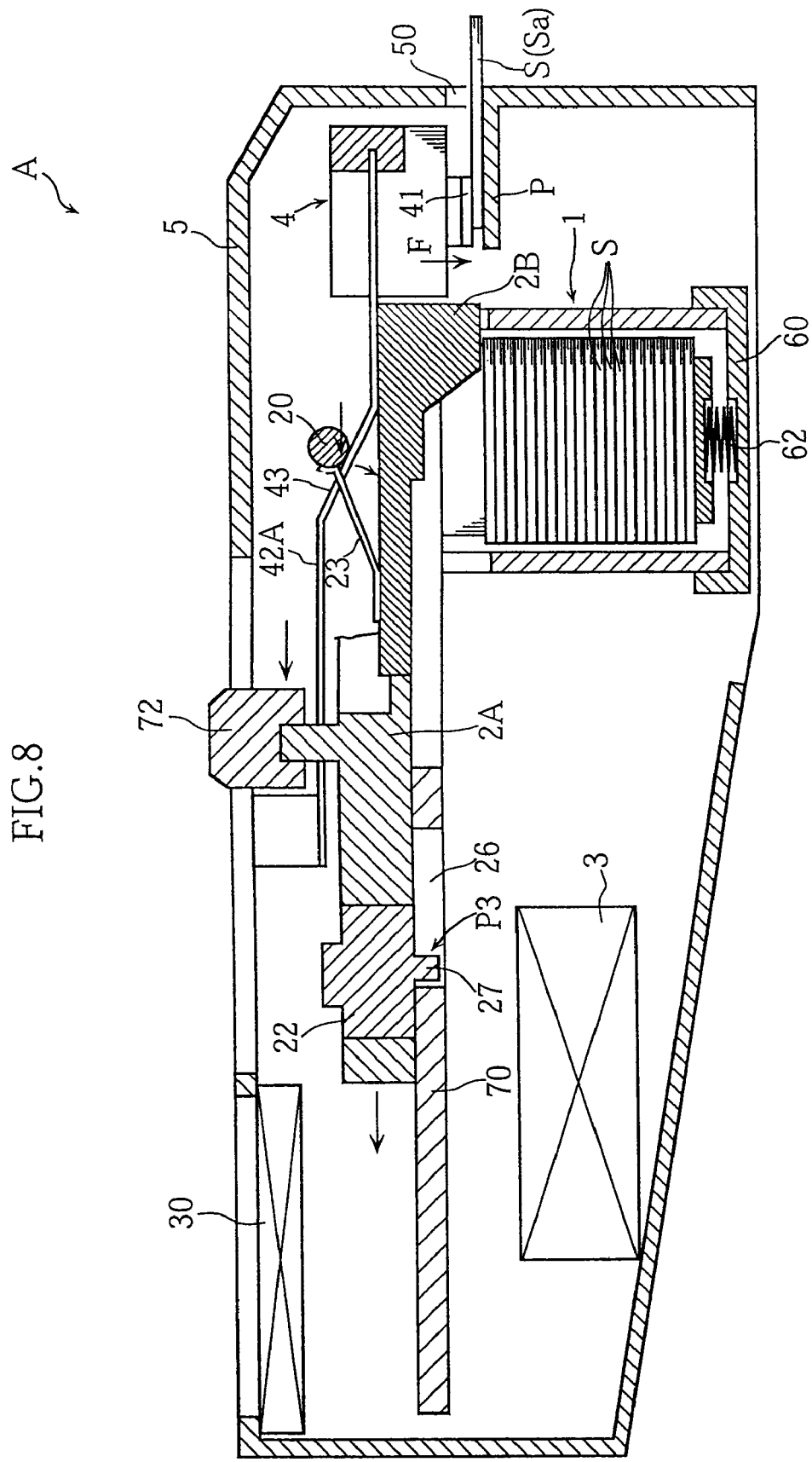
FIG. 8 is a simplified sectional view showing an action of the measuring instrument in FIG. 1.

As shown in FIG. 8, when the first and the second movable members 2A, 2B is moved rearward to bring the projection 27 to the third position P3, the pusher 20 pushes rearward the upper surface of the ramp 43 of the leaf spring 42a. (A part of the cam groove 26 shown in FIG. 8 is not the same part as a part of the cam groove 26 shown in FIG. 1, FIG. 6 or FIG. 7. This also applies to FIG. 9 and FIG. 10) The pushing force from the pusher 20 deforms the first leaf springs 42A downward, exerting a downward force F on the connector 4. This makes the terminals 41 of the connector 4 be pressed onto the electrodes of the sensor S (Sa), establishing reliable electrical connections. During the time in which such a pressing contact is present, the sensor S (Sa) is supplied with blood, and the measurement circuit 3 performs a measurement of glucose level in the blood.

Figure 9:
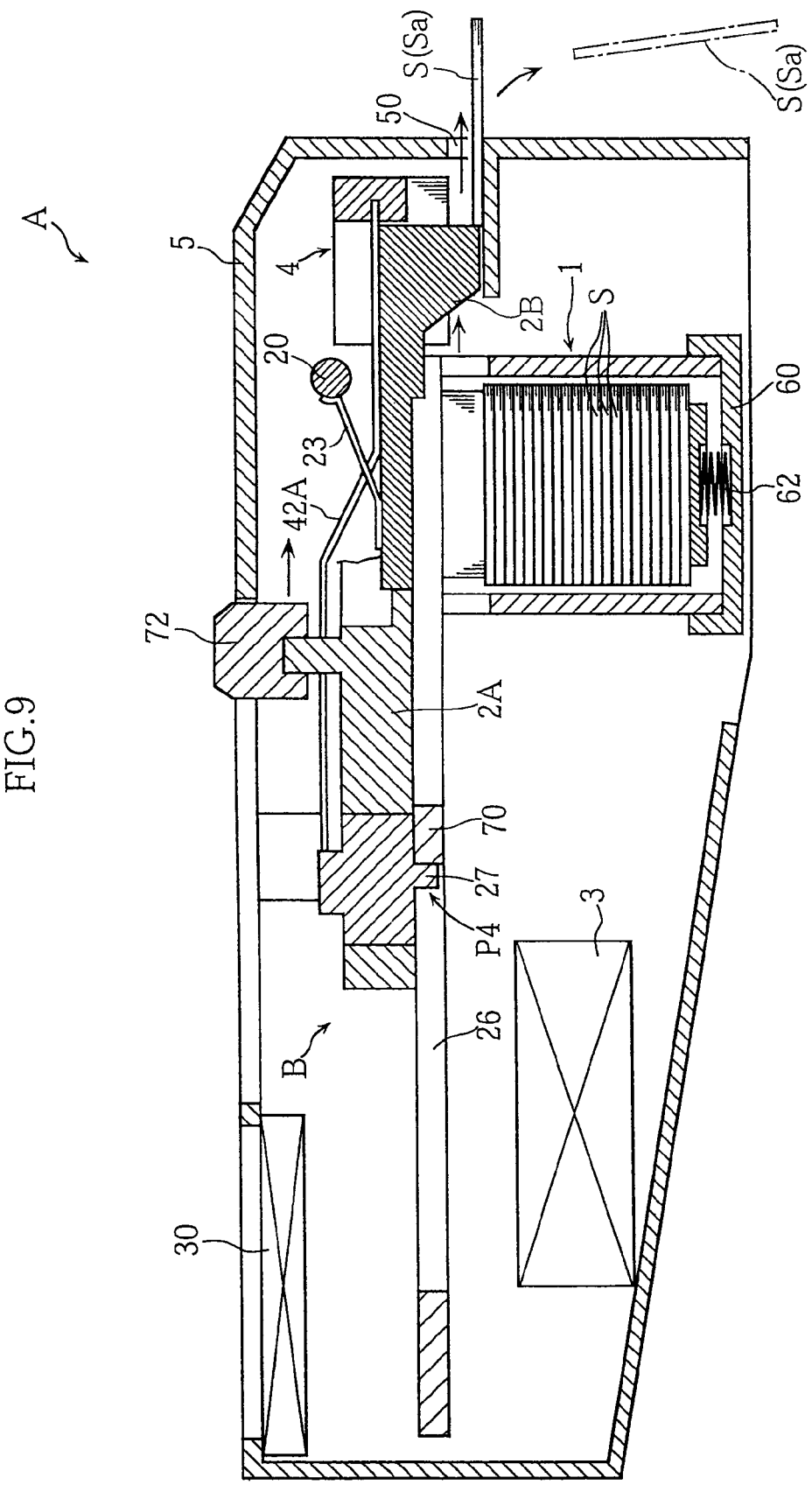
FIG. 9 is a simplified sectional view showing an action of the measuring instrument in FIG. 1.
Figure 10:
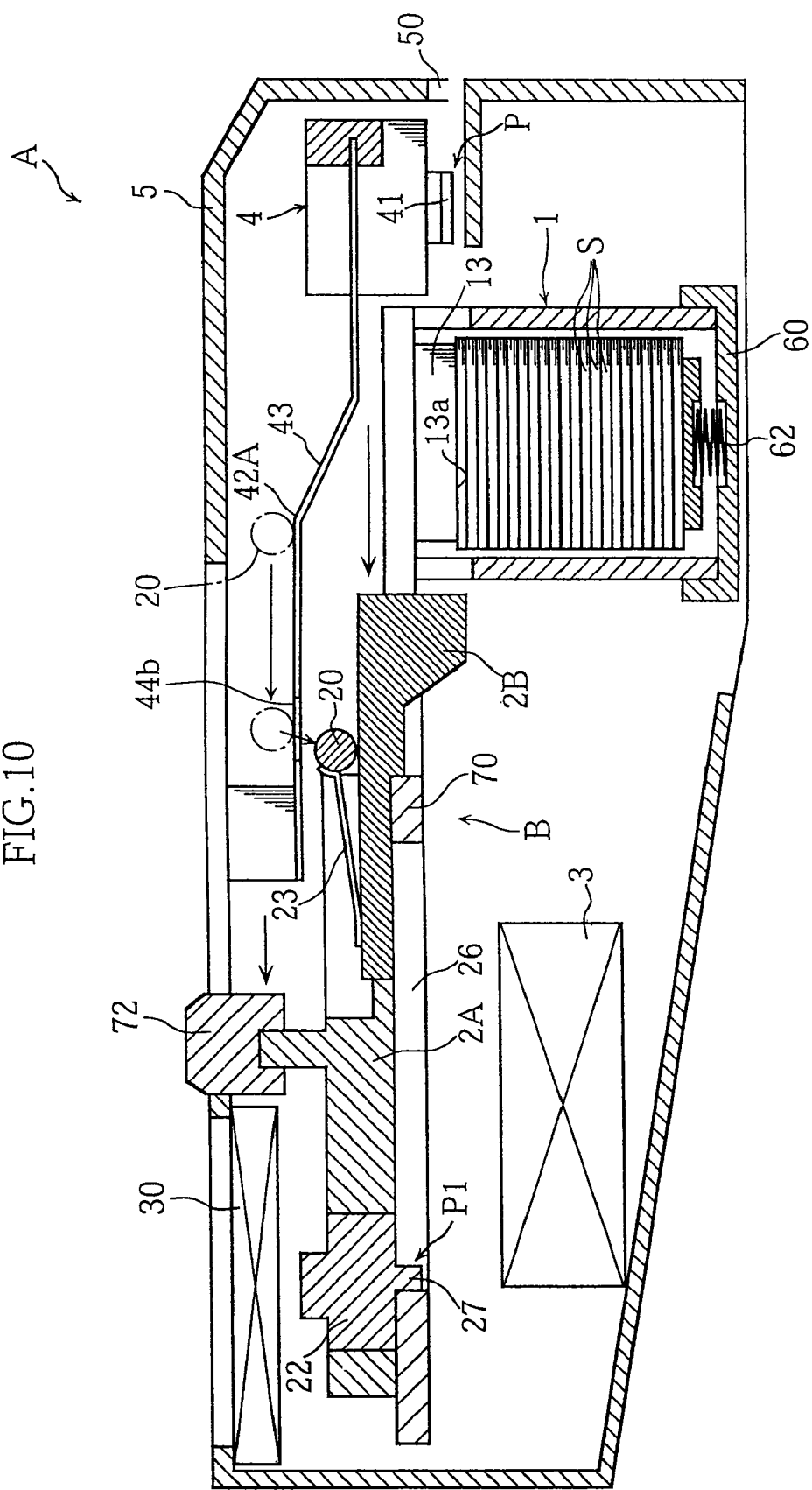
FIG. 10 is a simplified sectional view showing an action of the measuring instrument in FIG. 1.

As shown in FIG. 9, the operating tab 72 is forwarded again thereafter, which makes the second forward movement of the first and the second movable members 2A, 2B, causing the second movable member 2B to push the sensor S (Sa) out of the casing 5 from the opening 50. Therefore, the user can dispose of the sensor S(Sa) without touching the sensor S (Sa), which is preferable in terms of sanitation. After finishing the second forward movement, as shown in FIG. 10, it becomes possible to move the first and the second movable members 2A, 2B back to the initial positions. Since the pusher 20 is displaceable in vertical directions, when the first and the second movable members 2A, 2B make the rearward movement, it is also possible to have the pusher 20 pass above the first leaf springs 42A and the second cutouts 44b as indicated by phantom lines in the drawing, thereby having the pusher 20 come back to its initial position.

In the measuring instrument A according to the present invention, when the uppermost sensor S(Sa) of the sensors S stored in the storage 1 has been dispensed to the measuring position P, the remaining sensors S in the storage 1 are raised by the elastic urge from the spring 62, and a new uppermost sensor S(Sa) makes contact with the reference surfaces 13a. Therefore, this new uppermost sensor S (Sa) can also be dispensed as was the previous sensor S (Sa) described above, to the measuring position P by the action of the sensor dispensing mechanism B, and it is possible to repeat this cycle until all of the sensors S stored in the storage 1 have been used.

Figure 11:
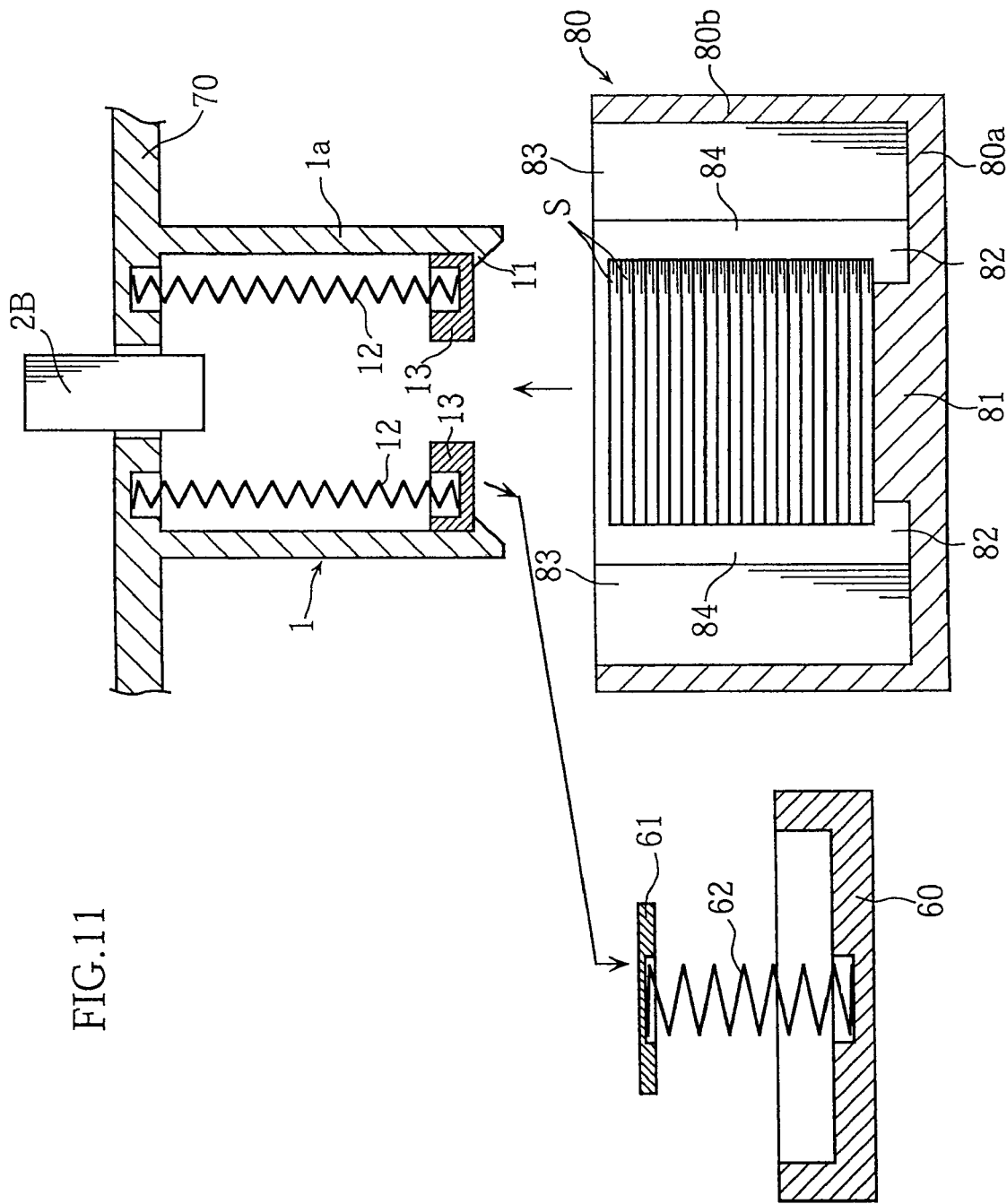
FIG. 11 is a sectional view of a primary portion, showing a sensor refilling operation.
Figure 12:
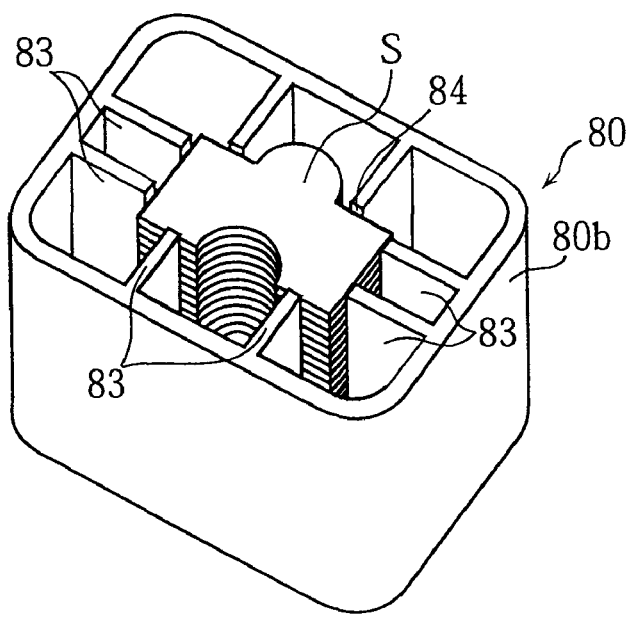
FIG. 12 is a perspective view of a case used for the sensor refilling operation.

A plurality of sensors S to be loaded into the storage 1 may be stored in a storage case 80 shown in FIG. 11 and FIG. 12.

The storage case 80, which includes a bottom 80a and a side wall 80b extending upward from the edge of the bottom 80a, has an upper opening. The bottom 80a has an upper surface with a center portion formed with a raised table 81, so that sensors S stacked thickness-wise can be placed on the table 81. The table 81 has a smaller area than the sensor S. Thus, the sensor S extends out of the table 81, leaving a space 82 below the sensors S. The space 82 accommodates the stoppers 11 as will be described later. Further, the storage case 80 is formed with a plurality of ribs 83 connecting to the bottom 80a and the side wall 80b. These ribs 83 are formed to surround a space in which sensors S are to be placed, so as to prevent the sensors S from being out of position and to maintain an orderly state of stacking. The sensors S do not contact the ribs 83, and the space provides a gap 84 for insertion of the wall 1a of the measuring instrument A. Preferably, the storage case 80 is a sealed case, with its upper opening normally closed and a dehumidifier placed within so that the sensors S will not be adversely affected by moisture.

Figure 13:
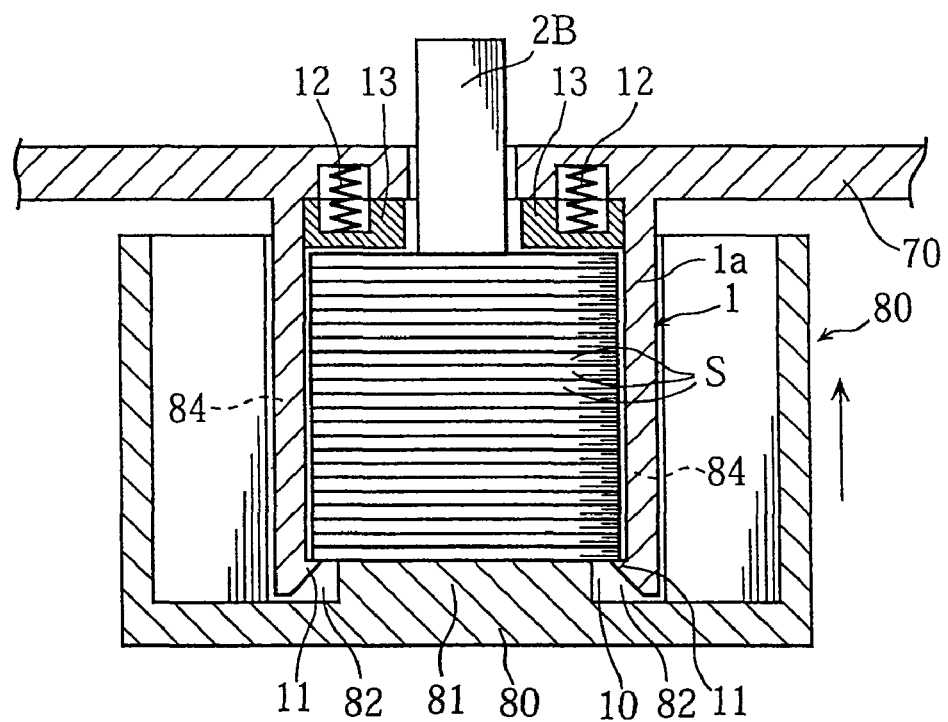
FIG. 13 is a sectional view of a primary portion, showing the sensor refilling operation.

After all of the sensors S in the storage 1 have been used, the storage 1 can be refilled with new sensors S in the following procedure for example:

First, as shown in FIG. 11, the lid 60 is removed from the bottom of the storage 1. Then, the spring 12 expands to lower the contact plates 13. Next, as shown in FIG. 13, the storage case 80 is placed around the storage 1 from below, to allow the wall 1a of the storage 1 to move into the gap 84 between the ribs 83 and the sensors S. This operation allows a plurality of sensors S in the storage case 80 to be loaded into the storage 1 from the insertion port 10 all at once against the elastic urge from the spring 12. The stoppers 11 can be placed in the space 82 below the sensors S, so it is possible to have the stoppers 11 come appropriately beneath the sensors S.

Figure 14:
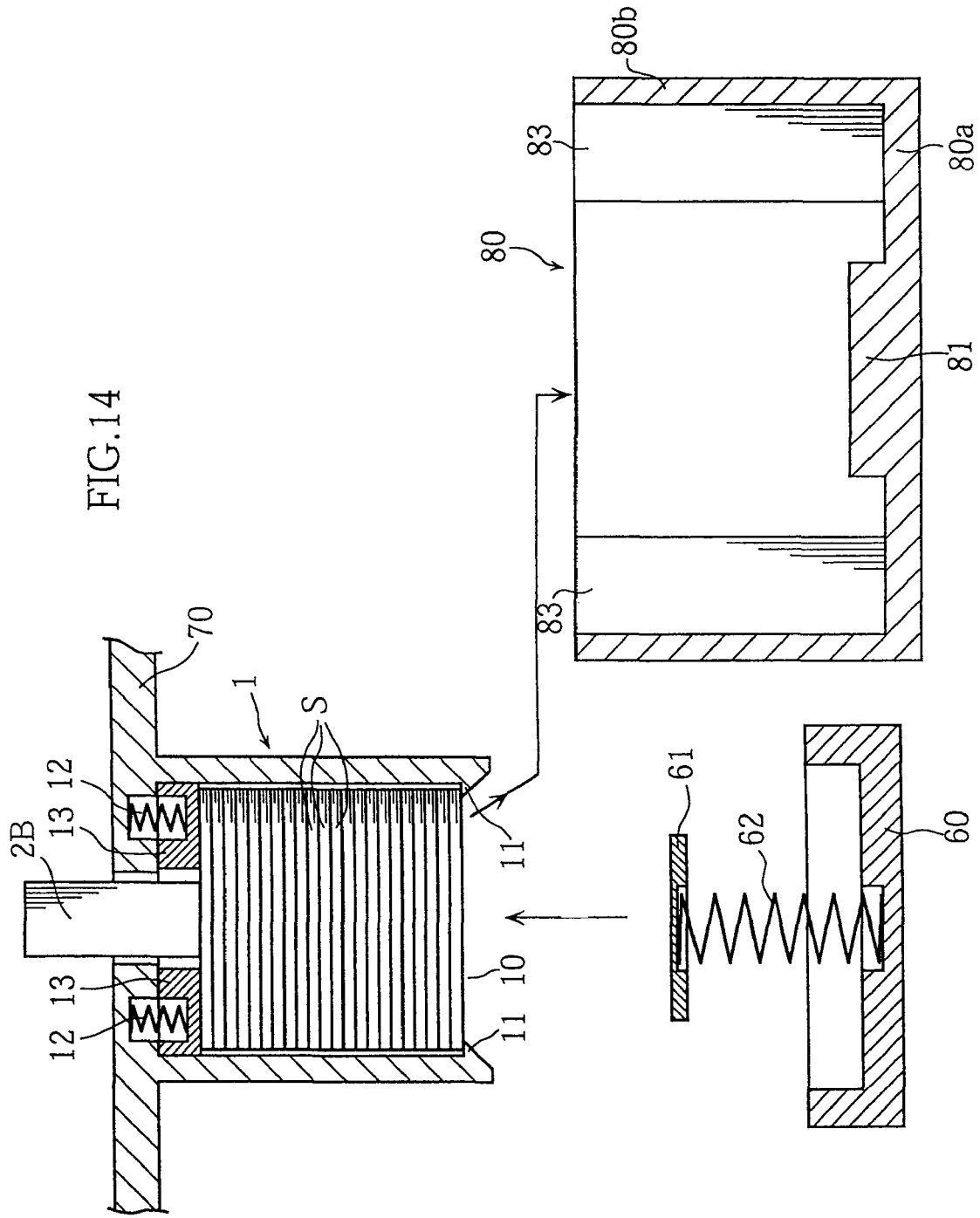
FIG. 14 is a sectional view of a primary portion, showing the sensor refilling operation.

Thereafter, as shown in FIG. 14, the storage case 80 is removed downwardly. During this action, the sensors S placed in the storage 1 are prevented by the stoppers 11 from dropping downward, and therefore remain loaded appropriately. After this, the lid 60 is replaced to the bottom of the storage 1.

Figure 15:
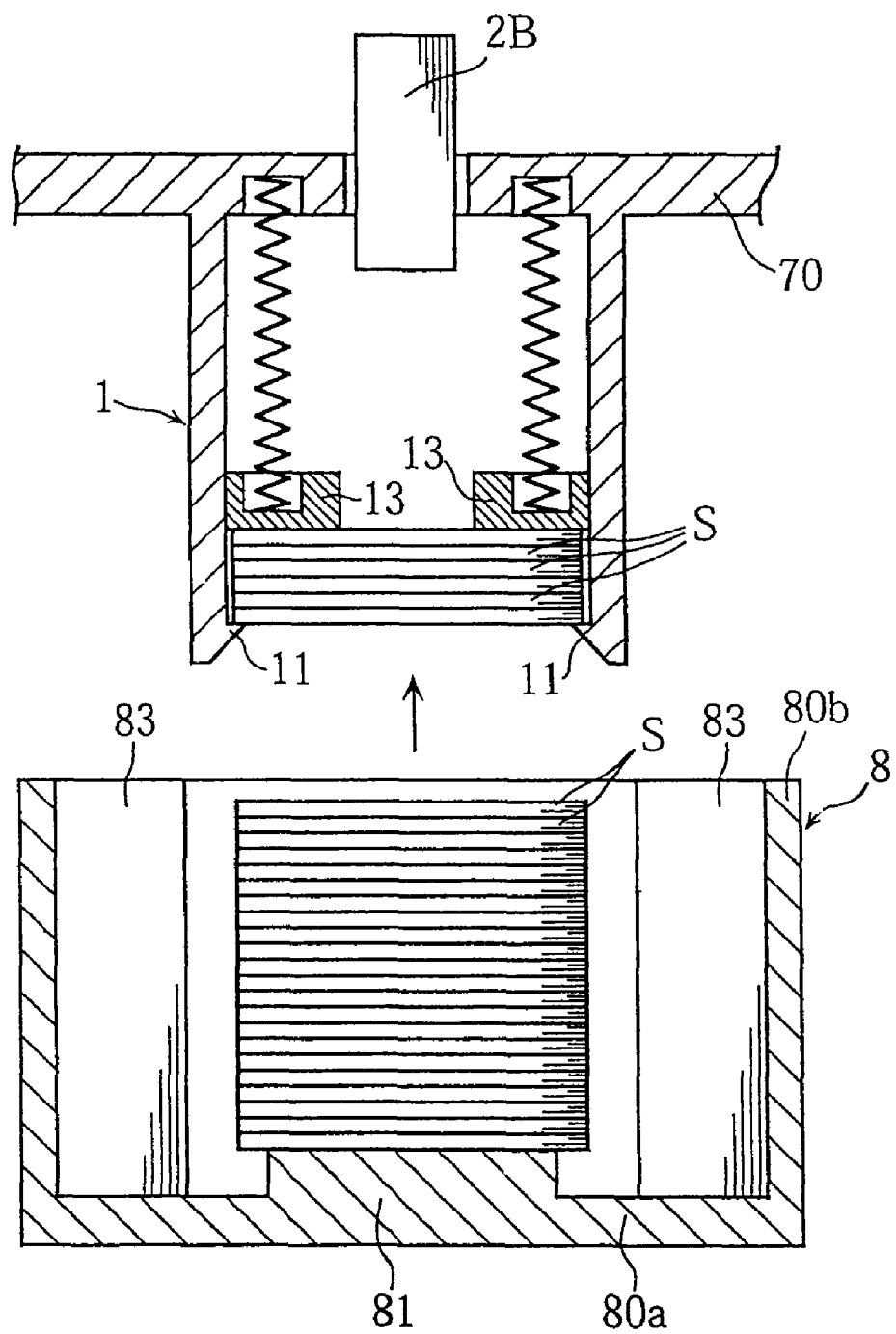
FIG. 15 is a sectional view of a primary portion, showing the sensor refilling operation.
Figure 16:
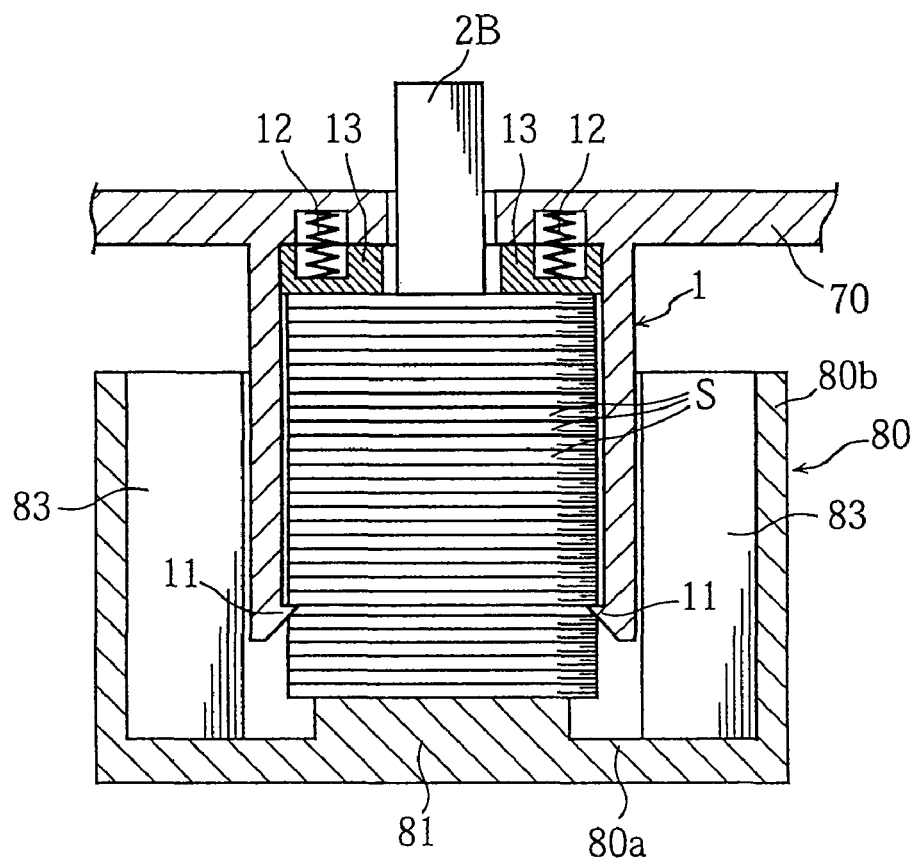
FIG. 16 is a sectional view of a primary portion, showing the sensor refilling operation.
Figure 17:
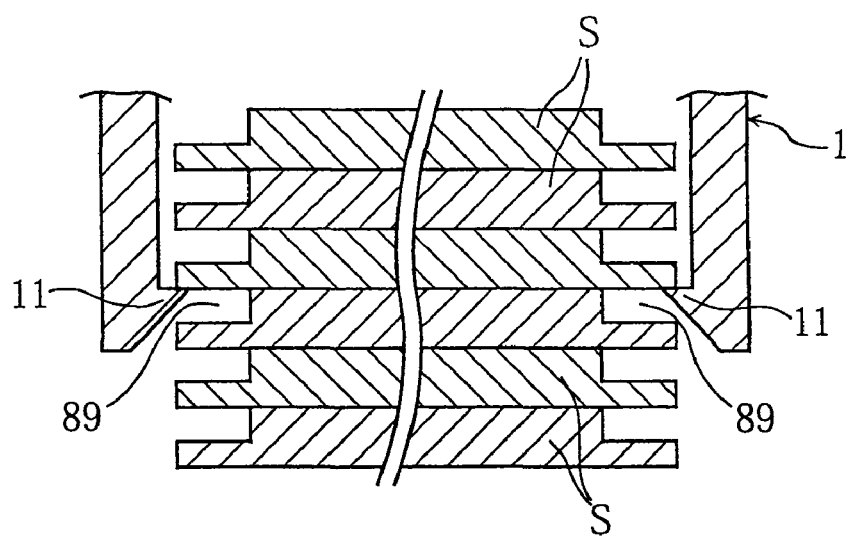
FIG. 17 is a sectional view of a primary portion, showing another refilling operation of the sensors.
Figure 18:
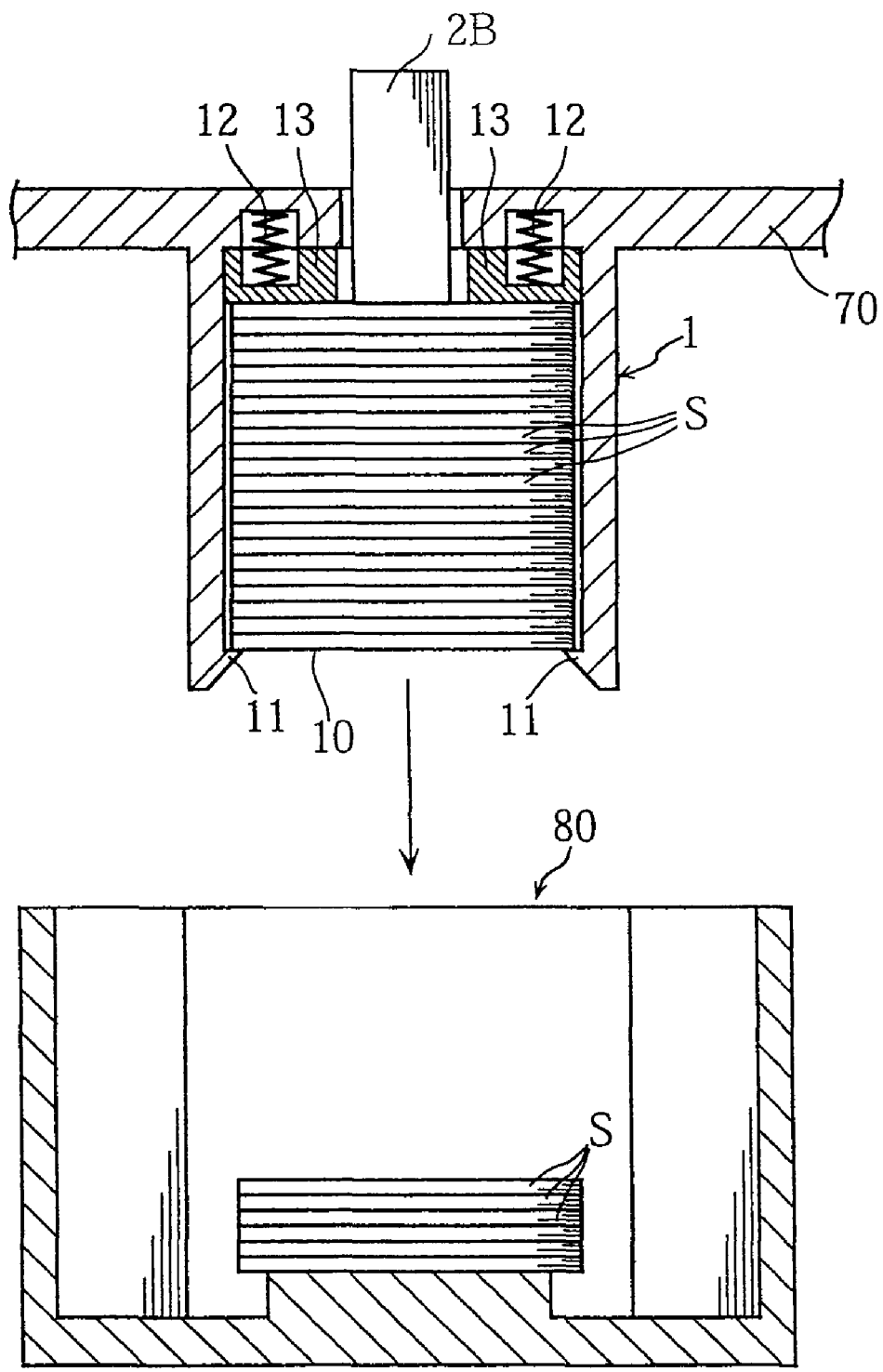
FIG. 18 is a sectional view of a primary portion, showing this refilling operation of the sensors.
Figure 19:
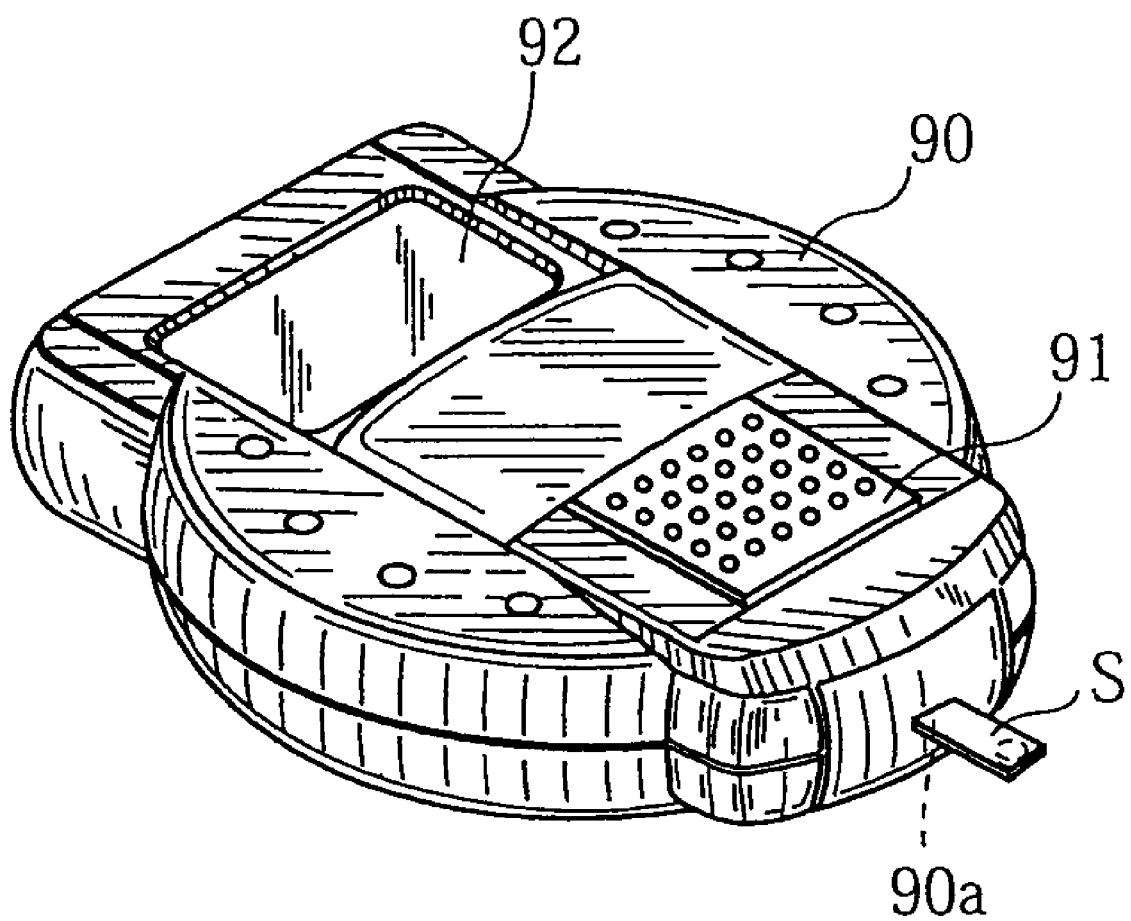
FIG. 19 is a perspective view of a conventional art.
Figure 20:
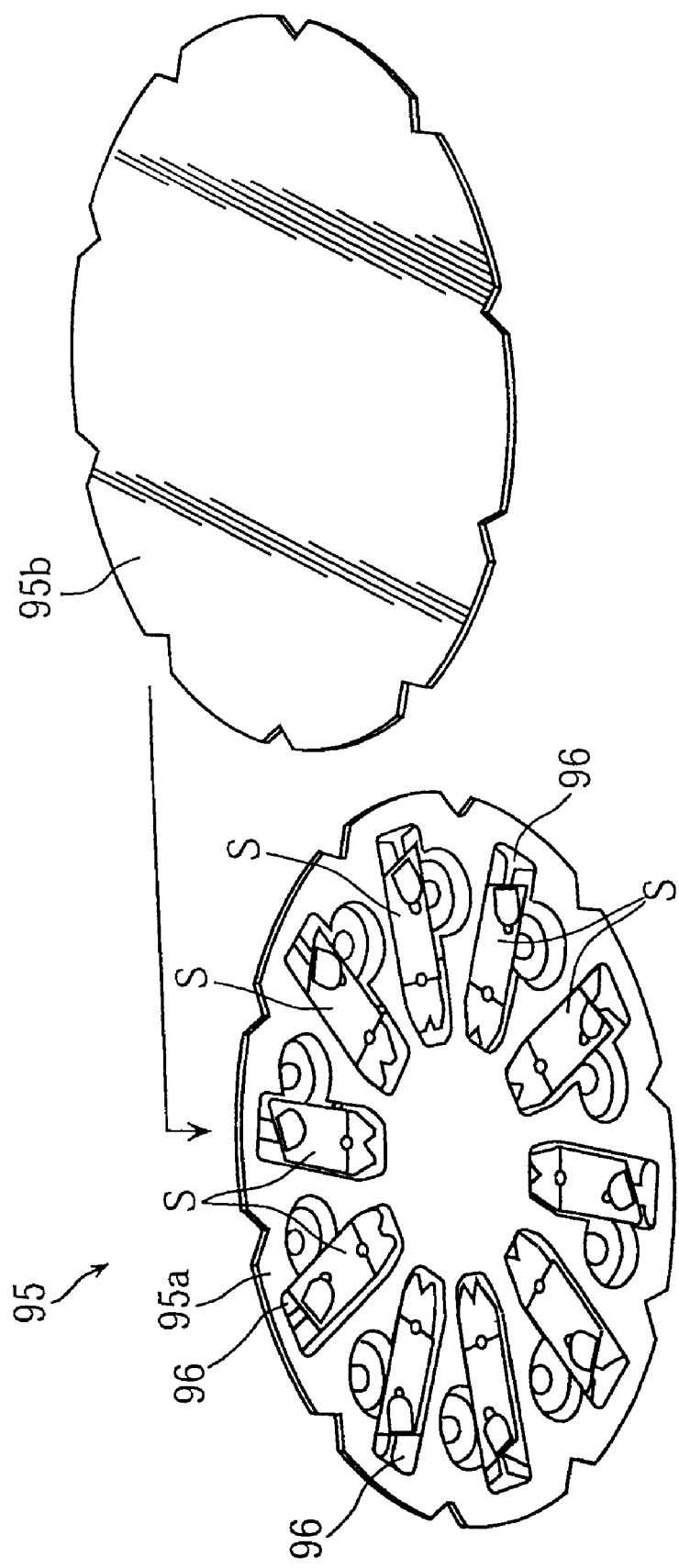
FIG. 20 is an exploded perspective view of a cartridge used in the conventional art.

The refilling operation of the sensors S described above is for a case when all of the sensors S in the storage 1 have run out. According to the measuring instrument A, as shown in FIG. 15 for example, it is also possible to replenish an appropriate number of sensors S so as to refill the storage 1 with the sensors S, even when the storage 1 still has one or more sensors S remaining. The refilling operation can be made as follows:

Specifically, in the status shown in FIG. 15, the storage case 80 is placed over the storage 1 in the same way as in the refilling operation described earlier, making the sensors S in the storage case 80 pushed into the storage 1, as shown in FIG. 16. The storage 1 can be refilled with the sensors S in this operation. During this, pawls of the stoppers 11 come between the sensors S in a lower portion of the storage 1. Preferably, as shown in FIG. 17, each sensor S has its edge portion made thinner than the center portion, so that there is a gap 89 between each pair of mutually adjacent sensors S. The gap 89 allows smooth entrance of the pawl of each stopper 11. Thereafter, as shown in FIG. 18, the storage case 80 is pulled out of the storage 1: The sensors above the stoppers 11 are prevented from dropping by the stoppers 11, so these sensors S are appropriately loaded in the storage 1.

As described, according to the measuring instrument A, it is easy to add sensors S to refill the storage 1 with the sensors S. Therefore, when the user leaves home for a long period of time for example, he may conveniently carry the measuring instrument A with the storage 1 filled with the sensors S.

Obviously, the storage 1 may not always be completely refilled with the sensors, but smaller and appropriate numbers of sensors S may be replenished. Further, according to the measuring instrument A, the sensors S in the storage 1 are used in a sequential order from the uppermost one, and the sequential order is the order in which the sensors S are loaded into the storage 1. This sufficiently eliminates an undesirable possibility that newer sensors are used before older sensors.

The present invention is not limited to what has been described in the embodiment above. Specific construction of each part and component of the measuring instrument according to the present invention may be varied in many ways.

The measuring instrument according to the present invention is not limited to those for measuring blood glucose levels, and can be made as measuring instruments for various kinds of targets in the medical field or other technical fields than medication. Therefore, there is no limitation to the kinds or specific construction of the measuring article.

The present invention places no limitation to a specific shape of the movable member which dispenses the measuring article loaded in the storage to a predetermined measuring position, or not limitation to a specific mechanism for moving the movable member. For example, manual operation may be replaced by an operation using a motor so that the movable member perform a predetermined action.

The invention claimed is:

1. A combination of a first storing case and a second storing case provided separately from the first storing case for storing a stack of measuring articles to be loaded in the first storing case,
    the first storing case comprising a lower end formed with an insertion port,
    the second storing case including a bottom for supporting the stack of measuring articles, a tubular side wall raised from an edge of the bottom, and an upper opening,
    at least one of the bottom and the side wall being provided with a series of ribs for maintaining an orderly stacked state of the measuring articles, and the stack of measuring articles stored in the second storing case being transferred from the second storing case into the first storing case when the lower end of the first storing case is inserted into the tubular side wall of the second storing case through the upper opening,
    wherein the ribs and the measuring articles define a clearance for insertion of the lower end of the first storing case, and
    wherein the lower end of the first storing case is formed with a stopper extending inwardly of the insertion port, the bottom of the second storing case being formed with a raised table for placement of the stack of measuring articles, the table having an area smaller than an area of each measuring article, the placement of the measuring articles on the table causing the measuring articles to overhang the table, forming a space beneath the overhang for the stopper entering said space to engage the stack of measuring articles from below.

2. The combination according to claim 1, wherein the lower end of the first storing case extends beyond a bottom surface of the stack of measuring articles when the lower end of the first storing case is inserted into the tubular side wall of the second storing case through the upper opening.

* * * * *